United States Patent [19]

Ramirez

[11] Patent Number: 5,415,315
[45] Date of Patent: May 16, 1995

[54] CLOSURE LID TO DISPOSABLE CONTAINER FOR HOLDING AND DISPOSING OF USED MEDICAL SHARPS AND OTHER MEDICAL-SURGICAL MATERIALS

[75] Inventor: Bruno J. Ramirez, Simi Valley, Calif.

[73] Assignee: Devon Industries, Inc., Chatsworth, Calif.

[21] Appl. No.: 123,141

[22] Filed: Sep. 17, 1993

[51] Int. Cl.$^6$ .............................................. B65D 83/10
[52] U.S. Cl. .................................. 220/346; 220/345; 220/908; 206/366; 206/370
[58] Field of Search ............... 220/256, 345, 346, 351, 220/900; 206/366, 370

[56] References Cited

U.S. PATENT DOCUMENTS

| | | | |
|---|---|---|---|
| 4,842,138 | 6/1989 | Sandel et al. | 220/345 X |
| 4,919,264 | 4/1990 | Shinall | 220/366 X |
| 4,955,477 | 9/1990 | Bruno | 220/908 X |
| 4,972,950 | 11/1990 | Shillington | 220/908 X |
| 5,082,137 | 1/1992 | Weinstein | 220/346 |
| 5,107,990 | 4/1992 | Wicherski et al. | 220/345 X |
| 5,273,161 | 12/1993 | Sagstetter | 220/908 X |

*Primary Examiner*—Steven M. Pollard
*Attorney, Agent, or Firm*—Poms, Smith, Lande & Rose

[57] ABSTRACT

A container lid for a medical storage-disposal container including a slide closure resistant to inadvertent movement from an open position into a fully closed and locked position. The container lid includes a top cover defining a disposal aperture and a laterally oriented depression. The slide closure contains a descending flange configured to engage the top cover depression and lock the slide closure in a fully closed position. An obstructing tab is pivotally coupled to the top cover and projects into the disposal aperture. The slide closure can only be moved into a fully closed and locked position if the obstructing tab is rotated into a non-obstructing orientation. The slide closure further includes protrusions on opposing lateral sides to require application of an affirmative force in order to displace the slide closure from a fully opened position. The slide enclosure further includes a plurality of straight sided apertures to facilitate removal of protective covers from hypodermic needles of varying size. The top cover further includes an aperture intersecting a tapering slot to facilitate removal of hypodermic needles of varying sizes from syringe bodies.

18 Claims, 4 Drawing Sheets

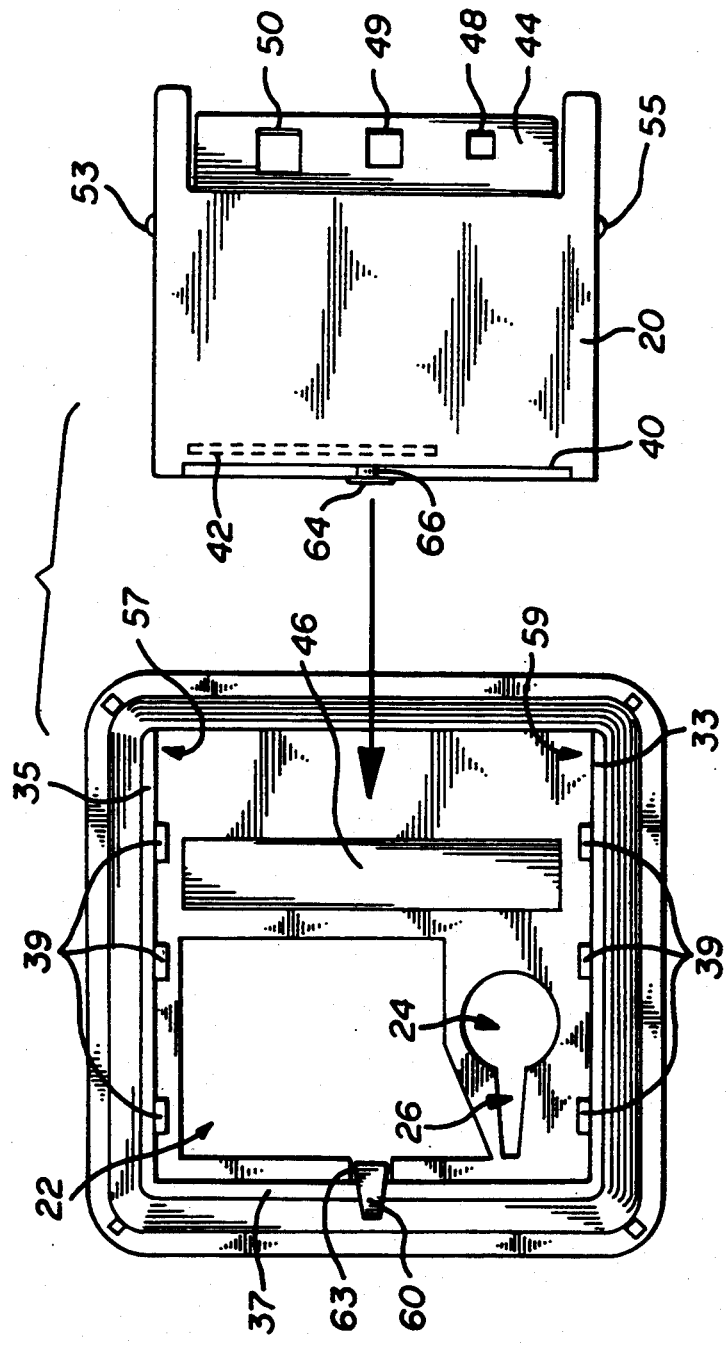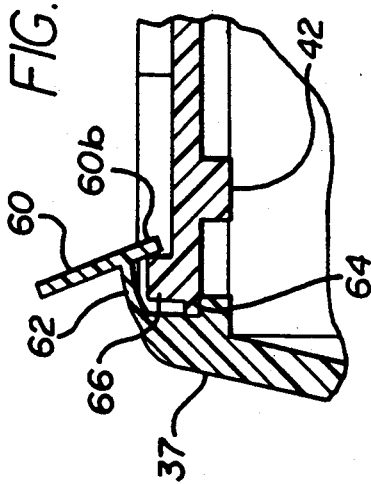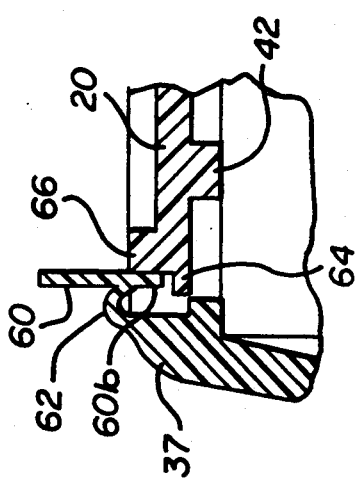

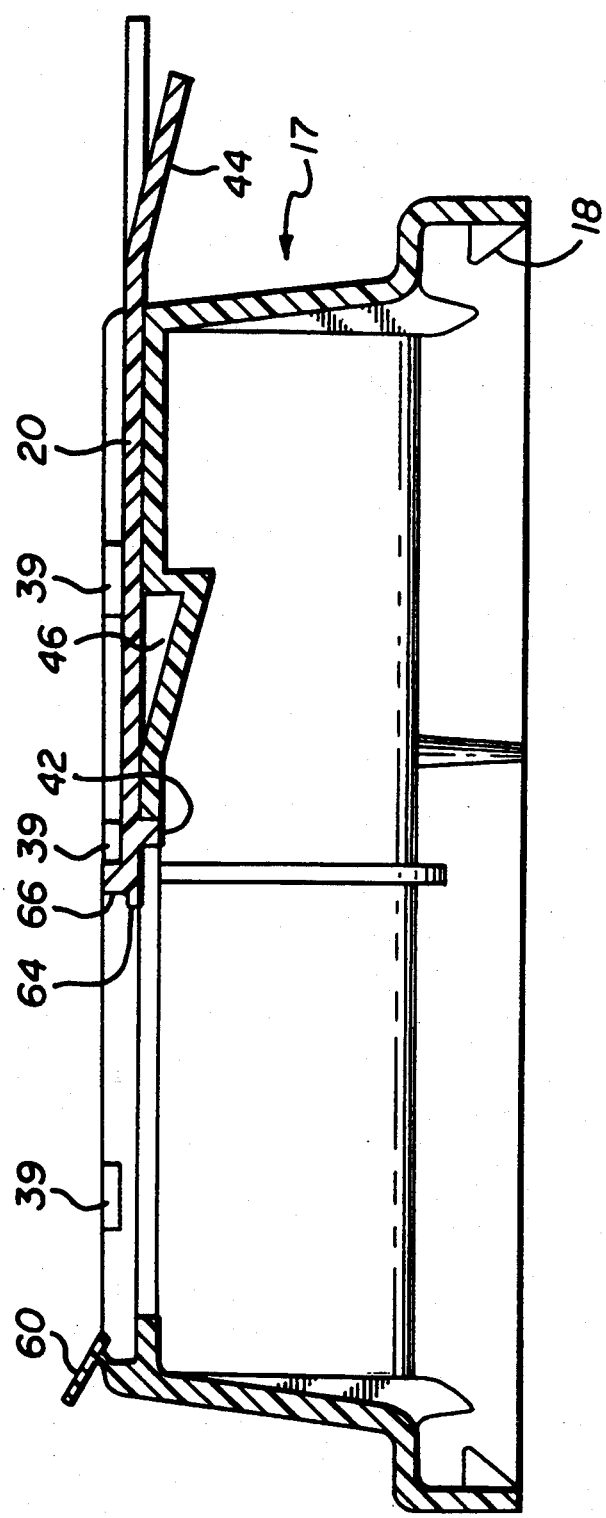
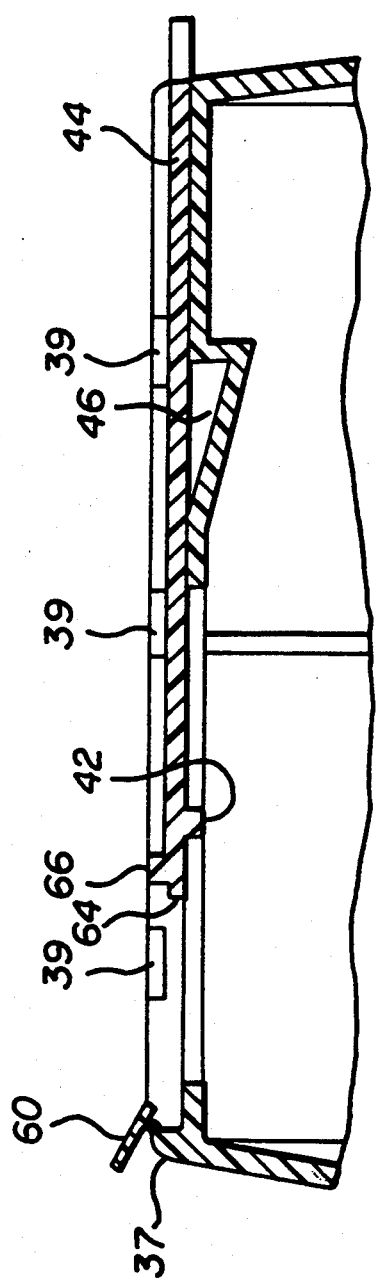
FIG. 4
FIG. 5

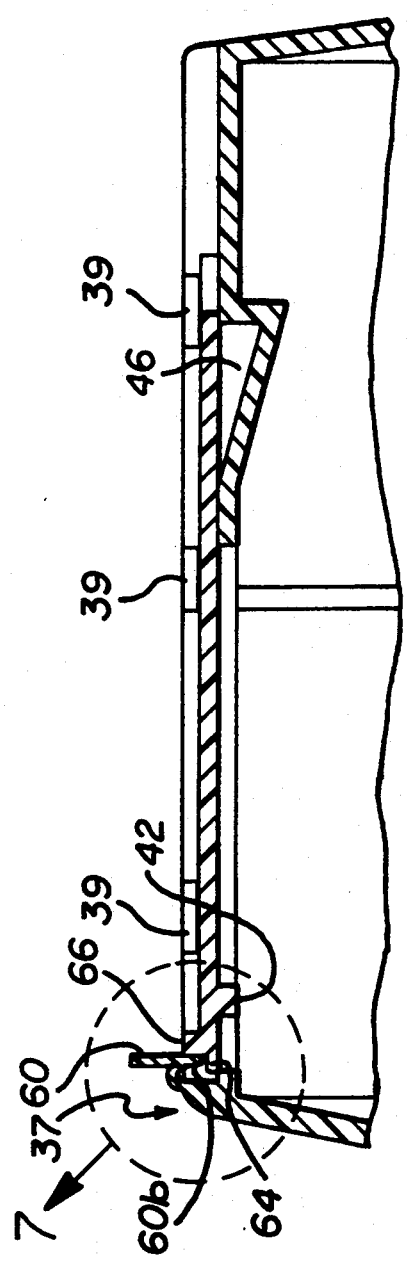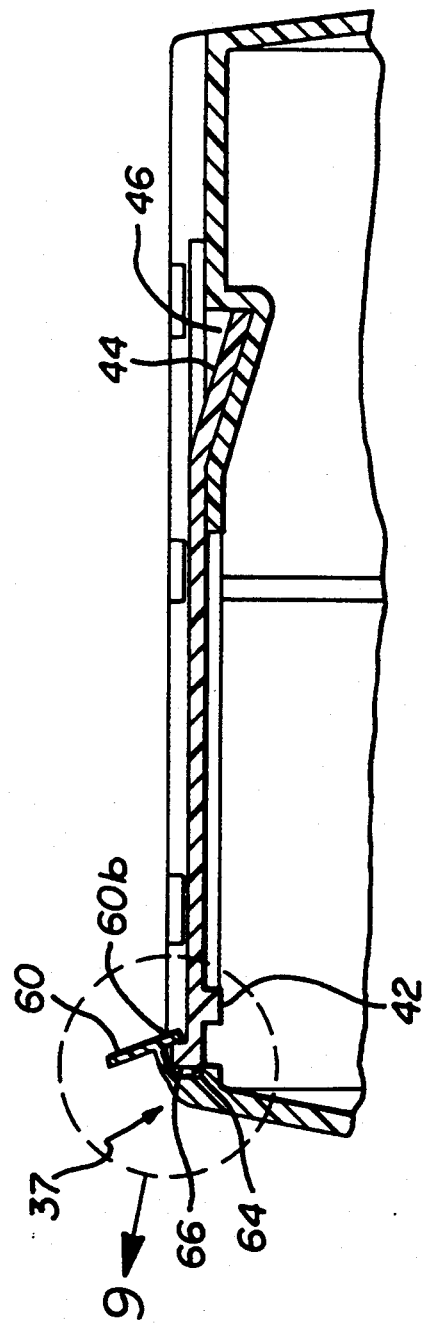

CLOSURE LID TO DISPOSABLE CONTAINER FOR HOLDING AND DISPOSING OF USED MEDICAL SHARPS AND OTHER MEDICAL-SURGICAL MATERIALS

BACKGROUND OF THE INVENTION

1. Field of the Invention

The present invention relates in general to medical-surgical supplies for hospitals and, more particularly, to disposable containers for used medical-surgical materials, including "sharps," such as hypodermic needles, suture needles and scalpel blades.

2. Summary of the Prior Art

This decade has seen an acceleration of a trend in the medical care provision field concerning the use of disposable, one-use medical-surgical devices and materials. This is a trend away from the former procedure of sterilization and reuse of these devices, both to reduce the high labor costs involved in the sterilization and to ensure that materials and devices used are completely sterile. Cost tradeoffs have shown this use-and-dispose philosophy compares quite favorable with the previous method.

Present hospital protocol in those institutions employing the use-and-dispose philosophy entails the assembly and distribution by unskilled personnel of a clean, but not sterilized, flexible plastic or paper container to those locations where containment is required, such as, operating rooms, nurses' stations, soiled linen rooms and emergency rooms. These containers may be used in the "sterile field" of the operating room, for example, on the "back table" when it is in the sterile field of the operating room or outside of the sterile field, where the "sterile nurse" passes the used materials to be disposed of to the "circulating nurse," who then disposes of the materials in the container.

After the containers are filled, they are typically collected by unskilled housekeeping personnel and taken for disposal. In some states this involves processing of the used materials by incineration, and in some states, by law, the materials are "red-bagged" or boxed, and stored for pickup by contract disposal personnel. They, in turn, transport the materials to be disposed to another location where they are autoclaved under low pressure steam for a predetermined time to sterilize them, then rebagged and taken to a landfill for burial.

Experience has taught that this disposal chain affords ample opportunity for unskilled personnel to be injured and/or contaminated by contact with used medical-surgical materials. Thus, a problem created by the use-and-dispose philosophy is that of containing and disposing of the used materials, much of which includes dangerously sharp implements referred to as "sharps" in the field, both within the hospital environment and in the disposal chain. Anther and related problem is the safe containment until disposal of those sharps which might be put to illicit uses, such as for example, hypodermic needles, were they to fall into unauthorized hands.

A number of storage and disposal containers have been developed to accommodate the use-and-dispose philosophy and alleviate the aforementioned disposal considerations. Exemplary thereof is the rigid disposable container of U.S. Pat. No. 4,842,138, issued Jun. 27, 1989 to Sandel, the disclosure of which is incorporated herein by this reference. In that invention, five plastic molded pieces were snapped together to form a single disposable container. Similarly, U.S. Pat. No. 5,107,990 issued Apr. 28, 1992 to Wicherski, et al., discloses another closure lid for a rigid disposable container configured to safely contain and dispose of medical-surgical materials. The disclosures of this latter patent are also incorporated herein by this reference. In the Wicherski, et al. invention, two lightweight plastic pieces form a container lid having a large opening for the insertion of used materials which can be permanently sealed by sliding a flush cover into a closed and locked position.

As useful as the Sandel and Wicherski, et al. containers are for the storage and disposal of used medical-surgical materials, there is still room for improvement. It would, for example, be advantageous to provide a medical-surgical disposal container with some mechanism for avoiding inadvertent closure or locking of the disposal opening. Accordingly, the present invention fulfills this and other needs.

SUMMARY OF THE INVENTION

Broadly, and in general terms, the present invention provides a closure lid suitable for use with medical-surgical disposal containers and having a number of novel and useful features, including a slide closure resistant to inadvertent displacement into a locked position. The present invention further provides a closure lid that is simply constructed and inexpensive, yet still able to prevent casual access to the contents of the container by unauthorized persons. The closure lid of the present invention can be used with conventional containers so as to prevent contamination of surrounding sterile areas, and yet is inexpensive enough to be disposed of simultaneously with the disposal of used medical-surgical materials, obviating the need to sterilize either the lid or the container itself.

In one embodiment of the container lid of the present invention includes a top cover with a slide closure, wherein the top cover defines a depression for the receipt of a corresponding depending flange of the slide cover. Positioning the slide cover in a fully closed position causes the depending flange to engage the depression in a locking position resistant to the opening of the slide closure without specialized tools or, alternatively, dismantling of the container. An obstructing tab is further flexibly mounted on a leading edge of the top cover to prevent the slide closure from being positioned into a fully closed and locked position unless the tab is intentionally pivoted into a non-obstructing position. The slide closure is also provided with protrusions, or berms, disposed along the sides of the slide closure so as to require affirmative force to displace the slide closure from a fully opened position. In accordance with another aspect of the present invention the top cover further includes an aperture and an intersecting tapered slot for engagement and removal from a syringe body of hypodermic needles of varying size, thus facilitating disposal of the needles within the container. The descending flap of the slide closure further defines a series of apertures of decreasing diameter. The apertures are configured to engage needle covers or sheathes filled over the end of a hypodermic syringe.

The novel features of the present invention will be better understood from the following detailed description, considered in connection with the accompanying drawings, wherein like numbers designate like elements. It should be expressly understood, however, that the drawings are for purposes of illustration and description

BRIEF DESCRIPTION OF THE DRAWINGS

FIG. 3 is an expanded top assembly view of the container lid and slide closure of the present invention;

FIG. 4 is a sectional side view of the container lid of the present invention shown along the sectional lines 4—4 of FIG. 1;

FIG. 5 is another sectional side view of the container lid of the present invention, with the slide closure partially closed;

FIG. 6 is a further sectional side view of the container lid of the present invention, with the closure lid almost fully closed;

FIG. 7 is an enlarged sectional view of a forward edge of the container lid of the present invention indicated in FIG. 6;

FIG. 8 is a sectional side view of the container lid of the present invention along the sectional lines 8—8 of FIG. 2; and FIG. 9 is an enlarged sectional view of a forward edge of the container lid of the present invention indicated in FIG. 8.

DETAILED DESCRIPTION OF THE PREFERRED EMBODIMENT

Figure 1:
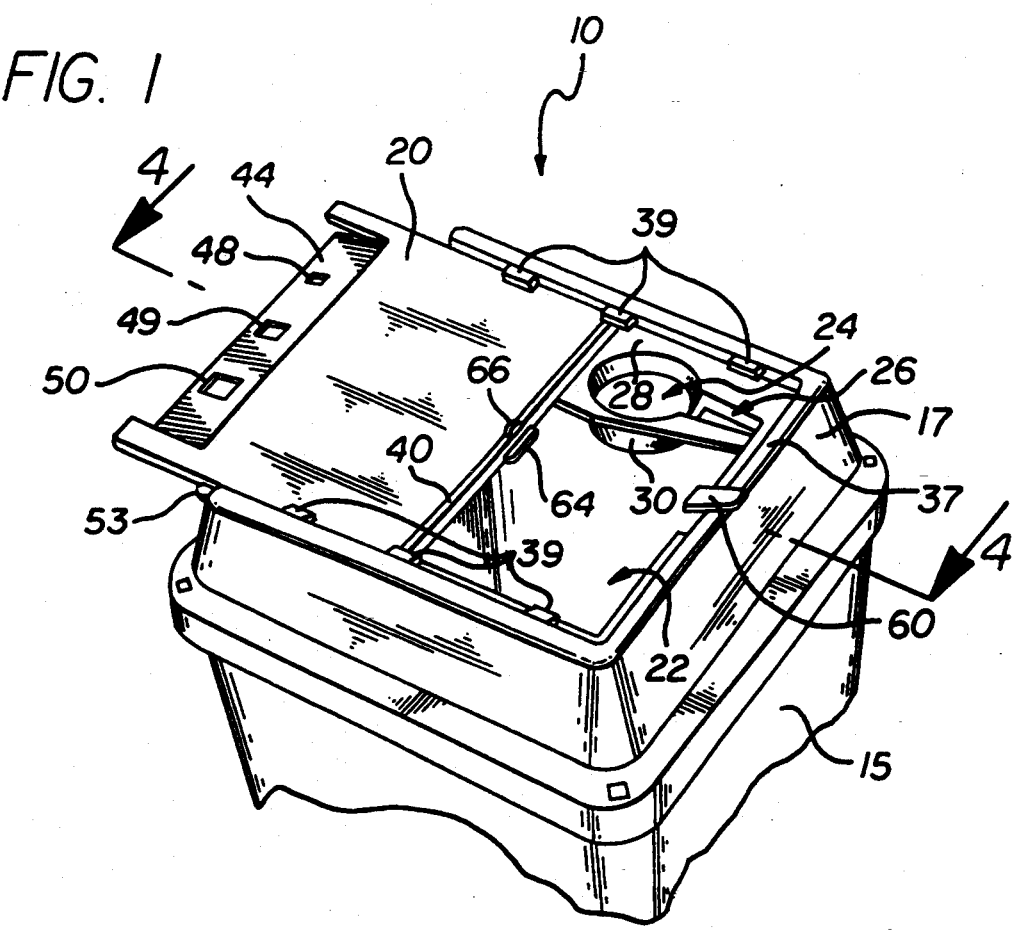
FIG. 1 is a perspective view of the container lid of the present invention attached to a rigid container body with the slide closure shown in a fully opened position.
Figure 2:
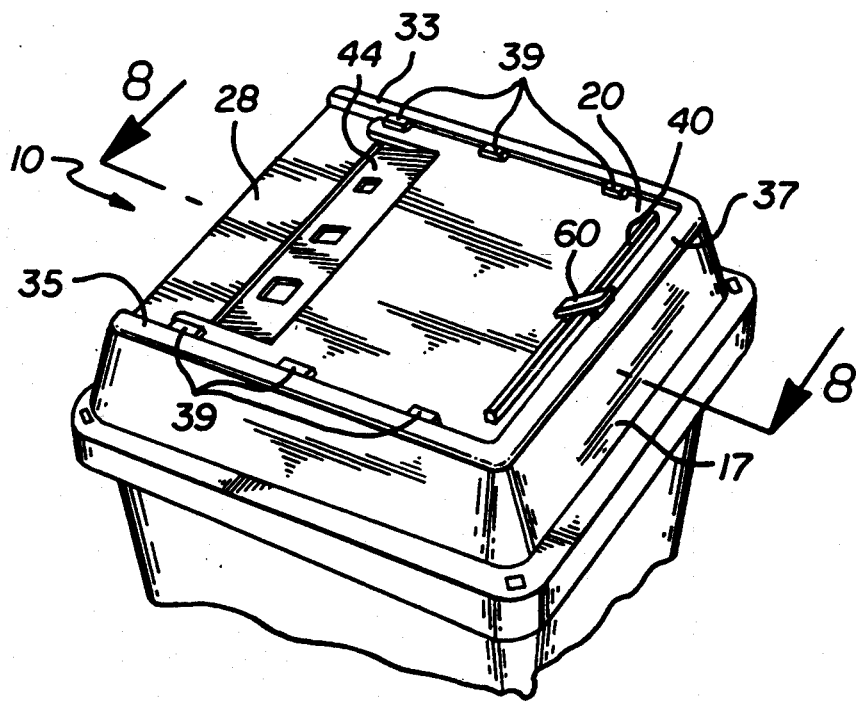
FIG. 2 is a perspective view of the container lid of the present invention with the slide closure shown in a fully closed and locked position.

Referring to the figures, and more particularly to FIGS. 1 and 2, there is shown one embodiment of the present invention, wherein a container lid 10 is attached to a container body 15. As best shown in FIGS. 1 and 3, the container lid 10 includes both a top cover 17 and slide closure 20. The container lid 10 and body 15 serve as a medical or surgical storage-disposal container for implements generally termed medical sharps. Such implements typically include hypodermic needles, suture needles, scalpel blades and the like. In the preferred embodiment, both the container lid 10 and body 15 are injection molded from strong but lightweight and inexpensive thermoplastics, such as polyethylene or polypropylene. This provides a container lid 10 that is relatively strong and rigid but sufficiently inexpensive to warrant one time use and then disposal. Additionally, the container lid 10 may be molded from transparent or translucent materials to provide for viewing of the contents of the container so that the remaining volume available for disposal of medical implements can be easily estimated. Injection molding of thermoplastic materials also permits the inclusion of details within the molds to incorporate within the parts certain advantageous features such as a nesting ability of the parts. The use of thermoplastic materials to form the container lid 10 further permits the inclusion of a smooth finish surface on both the inside and outside of the container, which helps to prevent the entrapment of potentially septic material on the internal or external surfaces of the container lid.

As shown in FIG. 4, the top cover 17 may be securely attached to the container body 15 by projecting ledges 18. These ledges 18 are preferably but not necessarily disposed, in the corners of the top cover 17. The projecting ledges 18 engage a protruding lip (not shown) common to a variety of container bodies so that, once attached, the top cover 17 cannot be easily removed from the container body 15 without the use of special tools or without damage to either the container lid 17 and/or container body 15.

Referring to FIGS. 1-3 the top cover 17 further includes both a first aperture 22 for the receipt of medical implements when the slide closure 20 is in an open position, and a second aperture including a generally circular opening 24 intersecting a tapering slot 26. This second aperture accommodates removal of Luer-type hypodermic needles from a syringe body. In use a hypodermic needle may be inserted into the circular opening 24 and positioned in the tapering slot 26 until rectangular portions of the hypodermic needle engage the walls of the slot 26. The syringe body can then be disengaged from the hypodermic needle by rotation of the syringe body with respect to the top cover 17 until the needle is released into the container body 15. The taper of slot 26 permits use of the opening 24 and slot 26 in the removal of hypodermic needles of varying size.

As further illustrated in FIG. 1, an upper surface 28 of the top cover 17 includes a descending ridge 30 about the edges of the circular opening 24 and tapering slot 26. This ridge 30 reinforces the portion of the top cover surface 28 adjacent the opening 24 and slot 26 so as to facilitate the use of considering twisting force for the removal of hypodermic needles beyond that otherwise available from the material forming the upper surface 28 of the top cover 17.

As further shown in FIGS. 1-3 the top cover 17 also includes raised lateral edges 33 and 35 on either side of the top cover surface 28 for preventing lateral displacement of the slide closure 20 with respect to the top cover 17. The top cover 17 further includes a raised leading edge 37 that abuts the slide closure 20 when the latter is in a fully closed position. The lateral edges 33 and 35 are in turn provided with ledges 39 to return the slide closure 20 in a sliding and engaging relationship with the top cover 17.

As further shown in FIGS. 1-3 and 5 the slide closure 20 includes a raised ledge 66 and a depending ledge 42 on a leading edge of the slide closure 20. The raised ledge 66 facilitates manipulation of the slide cover 20 from a fully opened to a fully closed position by a user. The depending ledge 42 prevents the slide cover 20 from being removed from the top cover 17 when the slide closure 20 is slid into a fully opened position. As shown in FIGS. 1-4 and 8, the slide closure 20 further includes a descending flap 44 to facilitate locking the slide closure 20 in a closed position by engaging a depression 46 formed in the top cover 17. As illustrated in FIG. 8 the descending flap 44 of the slide closure 20 fits into the depression 46 of the top cover 17 when the slide closure 20 is fully closed, thus preventing the slide closure 20 from being easily moved back into an open position without the use of specialized tools or dismantling of the container. Another novel and useful feature of the slide closure 20 concerns a series of square apertures 48, 49 and 50 formed in the descending flap 44 of the slide closure 20. These apertures 48-50 facilitate temporary storage of a hypodermic needle cover from a hypodermic needle, with the varying sizes of the apertures 48-50 accommodating hypodermic needle covers of varying size.

Still another novel aspect of the present invention concerns features of the top cover 17 and slide closure 20 intended to prevent inadvertent closure and locking of the slide closure 20 with respect to the top cover 17. As shown in FIGS. 1 and 3, for example, the slide cover 20 is provided with a pair of lateral protrusions or berms 53 and 55. Similarly, a pair of protrusions or berms 57 and 59 are provided on trailing edges of the raised lateral sides 33 and 35 of the top cover 17. When the slide cover 20 is in a fully opened position the berms 53 and 55 are located in an exposed position outside the lateral sides 33 and 35 of the top cover 17, adjacent the corresponding berms 57 and 59 of the top cover 17. Thus, protrusions 53 and 57 interfere with one another as the slide closure 20 moves towards the closed position, as do protrusions 55 and 59. Movement of the slide closure 20 from this fully opened position toward a partially closed position requires application of an affirmative force to urge the berms 53 and 55 of the slide closure 20 past the corresponding berms 57 and 59 of the top cover 17. Inadvertent displacement of the slide closure 20 from a fully opened position is thus avoided by requiring application of an affirmative force to displace the slide closure 20 from its fully opened position.

Several novel features of the container lid 10 are similarly directed to avoiding the inadvertent closure and locking of the slide closure 20 with respect to the top cover 17. As further illustrated in the figures, and particularly FIGS. 6-9, the top cover 17 includes an obstructing tab 60 with a pivotal coupling 62 attached to the leading edge 37 of the top cover 17. A portion 60b of this tab projects downward along the raised leading edge 37 of the top cover 17, and a notch 63 is also provided in the upper surface 28 of the top cover 17 to accommodate the tab portion 60b. The leading edge of the slide closure 20 is in turn provided with a forward projecting tab 64 and a raised ledge 66.

In operation, the slide closure 20 can only be moved into a fully closed and locked position, with the descending flap 44 of the slide closure 20 engaging the top cover depression 46 of the top cover 17, if the obstructing tab 60 is fully pivoted clear of the raised ledge 66 of the slide closure 20. If the obstructing tab 60 is simply left in its normal position, movement of the slide closure 20 towards the raised leading edge 37 of the top cover 17 causes the forward projecting tab 64 of the slide closure 20 to abut the tab portion 60b, thus pivoting the obstructing tab 60 into a position that guides the forward projecting tab 64 of the slide closure into the upper surface 28 of the top cover 17 and preventing the slide closure 20 from fully closing and locking. Thus only when the obstructing tab 60 is pivoted into a position to fully clear the raised ledge 66 of the slide closure 20 can the slide closure 20 be moved into a fully closed and locked position.

As further illustrated in FIG. 9, the above-described features further discourage or prevent inadvertent closure and locking of the slide closure 20 by requiring application of an affirmative force against the slide closure 20 to achieve a locking engagement of the flap 44 and the depression 46. When the obstructing tab 60 is fully pivoted into a non-obstructing orientation, the pivotal coupling 62 of the tab 60 still contacts the raised ledge 66 of the slide closure 20. The slide closure 20 cannot be urged into a fully closed and locked position unless an affirmative force is applied to the slide closure 20 so as to cause the raised ledge 66 of the slide closure 20 to displace the pivotal coupling 62.

These collective features of the top cover 17 and slide closure 20, directed to avoiding inadvertent closure of the slide closure 20, further substantially enhance normal use of the container lid 10. When a disposal container including the lid 10 of the present invention is in use, the slide closure 20 may remain in an open position to facilitate easy disposal of used surgical or medical implements, such a discarded hypodermic needles and other medical sharps. As discussed above, an affirmative force is required to displace the slide closure 20 from this fully opened position, thus avoiding inadvertent partial closure of the slide closure 20 and partial obstruction of the aperture 22.

The requirement of applying an affirmative force to dislodge the slide closure 20 from a fully open position, however, reduces the likelihood of an inadvertent partial closure of the slide cover 20. When the container is not in use, the slide closure 20 may be moved to a partially closed position with the forward projecting tab 64 of the slide closure 20 abutting the obstructing tab 60. With the tab 60 in this obstructing position, the slide closure 20 cannot be moved into a fully closed and locked position. Thus with the slide closure 20 in this position, however, the slide closure 20 still obstructs the circular opening 24 and tapering slot 26 of the top cover 17 and virtually the entirety of the aperture 22 of the top cover 17. Thus the slide closure 20 in this position prevents spillage of the contents of a container if the container is inadvertently tipped over or dropped onto the floor. Once the container is deemed full, or otherwise ready for disposal, the obstructing tab 60 may be pivoted into a non-obstructing position and the slide closure 20 urged into a fully closed and locked position by application of an affirmative force. Then, as discussed above, the slide closure 20 cannot be reopened without these special tools or the intentional dismantling of the container.

As can be seen from the above detailed description, the present invention provides a unique and highly useful container lid for the storage and disposal of used medical implements such as hypodermic needles and other medical sharps. Those skilled in the art will recognize that the foregoing materials, methods of fabrication and detailed features are suggested for illustration purposes only, and can by suitably modified to provide a variety of disposable container shapes, styles and functions without departing from the scope or spirit of the present invention. Accordingly, the scope of the present invention should not be limited to the particular embodiments discussed above, but should be defined only by the scope of the claims set forth below, and equivalents thereof.

What is claimed is:

1. A container lid for a medical disposal receptacle, comprising:

a top cover defining a disposal aperture and having a depression and a pair of side edges, at least one of said side edges including a cover protrusion; and a slide closure engaging the top cover substantially between said side edges, said slide closure having a descending flange projecting into the depression when said slide closure is fully closed, said slide closure being in a locked position when said descending flange projects into said depression, and a closure protrusion interfering with said cover protrusion as said slide closure moves towards said locked position, thereby preventing free movement of said slide closure, said closure protrusion and said cover protrusion being shaped such that they can be urged past one another as said slide closure moves towards said locked position and away from said locked position.

2. The container lid of claim 1, further comprising an obstructing tab pivotally attached to a forward edge of the top cover aperture and obstructing closure of the slide closure unless pivoted away from the slide closure.

3. The container lid of claim 2 wherein said slide closure includes a forward projecting ledge positioned opposite the obstructing tab and movement of the slide closure towards said locked position causes said ledge to pivot the obstructing tab into a position preventing the slide closure from locking.

4. The container lid of claim 2 wherein said slide closure includes an upward projection positioned opposite the obstructing tab and movement of the slide closure into said locked position requires application of an affirmative force to achieve displacement of a pivotal coupling of the obstructing tab.

5. The container lid of claim 1 wherein said slide closure includes a plurality of apertures having generally straight sides and said apertures facilitate removal of a hypodermic needle cover.

6. The container lid of claim 5 wherein said top cover includes a generally circular aperture intersecting a generally tapering slot and said aperture and slot facilitate removal of hypodermic needles of varying sizes from syringe bodies.

7. A container lid for a disposal receptacle, comprising:
   a top cover having a depression and defining a disposal aperture;
   a slide closure movably engaging said top cover and having a descending flange configured to project into said top cover depression when said slide closure is in a locked position; and
   an obstructing tab associated with said top cover, said obstructing tab being movable between a first position preventing movement of said slide closure into said locked position and a second position allowing movement of said slide closure into said locked position.

8. The container lid of claim 7 wherein said slide closure includes a forward projecting ledge positioned opposite the obstructing tab and movement of the slide closure towards said locked position causes said ledge to pivot the obstructing tab into said first position, thereby preventing the slide closure from locking.

9. The container lid of claim 7 wherein said slide closure includes an upward projection positioned opposite the obstructing tab and movement of the slide closure into said locked position requires application of an affirmative force to achieve displacement of a pivotal coupling of the obstructing tab.

10. The container lid of claim 7 wherein said slide closure includes protrusions disposed on lateral sides of the slide closure and an affirmative force is required to displace the slide closure from a fully opened position.

11. The container lid of claim 7 wherein said slide closure includes a plurality of apertures having generally straight sides and said apertures facilitate removal of a hypodermic needle cover.

12. The container lid of claim 7 wherein said top cover includes a generally circular aperture intersecting a generally tapering slot and said aperture and slot facilitate removal of hypodermic needles of varying sizes from syringe bodies.

13. A container lid for a disposal receptacle, comprising:
   a top cover having a depression and defining a disposal aperture; and
   a slide closure slidably engaging said top cover and having a main portion adapted to cover said disposal aperture and a descending flange movable between a first position substantially coplanar to said main portion and a second position projecting into said depression when said slide closure is fully closed thereby locking said slide closure, said descending flange being biased towards said second position.

14. The container lid of claim 13, further comprising a pivotal tab flexibly attached to a forward edge of the top cover aperture and obstructing closure of the slide closure unless pivoted away from the slide closure.

15. The container lid of claim 14 wherein said slide closure includes a forward projecting ledge positioned opposite said pivotal tab and movement of the slide closure towards a closed position causes said ledge to rotate the tab into an obstructing position preventing the slide closure from locking.

16. The container lid of claim 14 wherein said slide closure includes an upward projection positioned opposite said tab and movement of the slide closure into a fully closed and locked position requires application of an affirmative force to achieve displacement of a flexible coupling of the top cover tab.

17. The container lid of claim 13 wherein said slide closure includes protrusions disposed on lateral sides of the slide closure and an affirmative force is required to displace the slide closure from a fully opened position.

18. The container lid of claim 13 wherein said slide cover includes a plurality of apertures having generally straight sides and said apertures facilitate removal of a hypodermic needle cover.

* * * * *